(12) United States Patent
Ren et al.

(10) Patent No.: US 9,182,332 B2
(45) Date of Patent: Nov. 10, 2015

(54) DEVICE AND METHOD FOR TESTING CORROSION INHIBITOR

(71) Applicant: Nanjing University, Nanjing (CN)

(72) Inventors: Hongqiang Ren, Nanjing (CN);
Zhanhui Shen, Nanjing (CN); Jinju Geng, Nanjing (CN); Ke Xu, Nanjing (CN); Xinkun Ren, Nanjing (CN)

(73) Assignee: Nanjing University, Nanjing (CN)

( * ) Notice: Subject to any disclaimer, the term of this patent is extended or adjusted under 35 U.S.C. 154(b) by 374 days.

(21) Appl. No.: 13/872,112

(22) Filed: Apr. 28, 2013

(65) Prior Publication Data

US 2013/0284597 A1    Oct. 31, 2013

(30) Foreign Application Priority Data

Apr. 28, 2012    (CN) .......................... 2012 1 0130590

(51) Int. Cl.
*G01N 27/403*    (2006.01)
*G01N 27/26*    (2006.01)
*G01N 17/02*    (2006.01)

(52) U.S. Cl.
CPC ...................................... *G01N 17/02* (2013.01)

(58) Field of Classification Search
CPC ................................ G01N 17/02; G01N 17/04
See application file for complete search history.

(56) References Cited

U.S. PATENT DOCUMENTS 5,370,776 A * 12/1994 Chen ........................ 205/776.5

FOREIGN PATENT DOCUMENTS

JP    09-329567 A  *  12/1997  ............. G01N 27/26
SU    1019292 A    *   5/1983  ............. G01N 17/00

OTHER PUBLICATIONS

JPO computer-generated English language translation of the Claims and Detailed Description of JP 09-329567 A, patent published Dec. 9, 1997.*
EPO computer-generated English language translation of SU 1019292 A, patent published Feb. 18, 1982.*

* cited by examiner

*Primary Examiner* — Alexander Noguerola
(74) *Attorney, Agent, or Firm* — Matthias Scholl P.C.; Matthias Scholl

(57) ABSTRACT

A device for testing a corrosion inhibitor, the device including: a circulating cooling water tank; a circulating water pump; a flowmeter; a five-port glass tube; a working electrode; a reference electrode; an auxiliary electrode; a heating rod; and an electrochemical workstation. The circulating water pump is connected to the circulating cooling water tank. The heating rod is fixed inside the circulating cooling water tank. The water inlet of the flowmeter is connected to the circulating water pump. The water outlet of the flowmeter is connected to the water inlet of the five-port glass tube. The water outlet of the five-port glass tube is connected to the circulating cooling water tank. The working electrode the reference electrode, and the auxiliary electrode are connected to the electrochemical workstation; and the electrochemical workstation is connected to a host computer.

7 Claims, 2 Drawing Sheets

DEVICE AND METHOD FOR TESTING CORROSION INHIBITOR

CROSS-REFERENCE TO RELATED APPLICATIONS

Pursuant to 35 U.S.C. §119 and the Paris Convention Treaty, this application claims the benefit of Chinese Patent Application No. 201210130590.0 filed Apr. 28, 2012, the contents of which are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to the evaluation of a corrosion inhibitor, and more particularly to a device and a method for evaluating a corrosion inhibitor for a circulating cooling water system.

2. Description of the Related Art

Typical methods for evaluating the performance of a corrosion inhibitor include an electrochemical method and a rotary coupon method.

The polarization curve method and the linear polarization resistance method, which belongs to the electrochemical method, are the most commonly used steady state electrochemical test methods. Besides, the transient test method including an AC impedance spectroscopy test has been developed and widely used. However, the current electrochemical method requires preparing a corrosive solution to be tested, such as a certain concentrated sulfuric acid solution, a hydrochloric acid solution, and a sodium chloride solution. A certain amount of the corrosive solution to be tested is then input into a three-port flask, and the corrosion of the corrosive solution to a metal is tested by using a three-electrode system in a static state. In such a system, a surface of the electrode is not washed by the water flow, but the cooling water in the circulating cooling water system flows through surfaces of a pipe and a device at a certain flow velocity and has a shearing action on the surfaces of the device and the pipe; furthermore, the solute is evenly distributed in the water. However, for electrochemical test in the laboratory, the electrode surface is not able to simulate a hydraulic condition on the surfaces of the pipe and device of the circulating cooling water system. Thus, concentration polarization easily occurs, which affects the accuracy of the testing result. Furthermore, the AC impedance spectroscopy method employs the three-electrode system and has a high requirement on the relative position of the electrodes, which causes difficulty for the installation of the three-electrode system on the circulating cooling water system.

The rotary coupon method is a common method for testing a corrosive ability. The method includes: immersing a test piece into a prepared solution for testing, rotating the solution for 72 hours; removing a rust resulting from the corrosion from the test piece, calculating a corrosion rate by a decreased weight of the test piece, and calculating a corrosion efficiency based on the corrosion rate in the presence of a corrosion inhibitor or without a corrosion inhibitor. The method is capable of directly reflecting the corrosion condition, and is very close to an actual working condition. However, the method is disadvantageous in that treatments of the test piece are necessitated before and after the corrosion, thus, errors are easily produced because of lots of human factors. Furthermore, the method is time consuming, and the testing solution reduces because of evaporation during the testing period; thus, the solution needs to replenish, which is inconvenient.

Conventional devices and methods for evaluating a corrosion inhibitor is capable of simulating the corrosion of the liquid and the condensed gas liquid on a pipe and a device at the same time, solving the problem that the pipe and the device in the industry are subject to the corrosion of both the liquid and the condensed gas liquid but the corrosion thereof are not able to be measured at the same time. The device is not capable of simulating the surface hydraulic condition in the circulating cooling water system. And the rotary coupon method requires treatments on the test piece before and after the corrosion test, thereby resulting in errors because of human factors. Besides, the improvement is desired on the capacity of simulating the hydraulic condition of the surfaces of the device and the pipeline in actual systems.

SUMMARY OF THE INVENTION

In view of the above-described problems, it is one objective of the invention to provide a device for evaluating a corrosion inhibitor for a circulating cooling water system. The device is provided with a five-port glass tube capable of simulating a hydraulic condition of the circulating cooling water and fixing the three electrodes. The device and the method of the invention achieve a good combination of the method for testing the AC impedance spectroscopy and testing condition of dynamic circulating cooling water. The device is capable of simulating the temperature and the flow velocity of the circulating cooling water system, and can fast evaluate the corrosion inhibition performance of the corrosion inhibitor.

To achieve the above objective, in accordance with one embodiment of the invention, there is provided a device for evaluating a corrosion inhibitor for a circulating cooling water system, comprises: a circulating cooling water tank; a circulating water pump; a flowmeter, the flowmeter comprising a water inlet and a water outlet; a five-port glass tube, the five-port glass tube comprising a water inlet, a water outlet, a working electrode port, a reference electrode port, and an auxiliary electrode port; a working electrode; a reference electrode; an auxiliary electrode; a heating rod; and an electrochemical workstation. The circulating water pump is connected to the circulating cooling water tank via a first pipe. The heating rod is fixed inside the circulating cooling water tank. The water inlet of the flowmeter is connected to the circulating water pump; and the water outlet of the flowmeter is connected to the water inlet of the five-port glass tube via a second pipe. The working electrode, the reference electrode, and the auxiliary electrode are mounted in the working electrode port, the reference electrode port, and the auxiliary electrode port, respectively. The water outlet of the five-port glass tube is connected to the circulating cooling water tank via a third pipe. The working electrode, the reference electrode, and the auxiliary electrode are connected to the electrochemical workstation. The electrochemical workstation is connected to a host computer.

In a class of this embodiment, the five-port glass tube is a glass tube having a diameter between 20 and 30 mm and a length between 300 and 500 mm. The water inlet and the water outlet of the five-port glass tube are arranged on two horizontal ends of the five-port glass tube, and the water inlet and the water outlet of the five-port glass tube have a diameter between 10 and 20 mm and a length between 30 and 50 mm. The reference electrode port and the auxiliary electrode port are arranged on one side of the five-port glass tube. A distance between a branch pipe of the reference electrode port and a branch pipe of the auxiliary electrode port is 10-30 mm. The working electrode port is arranged on the other side of the five-port glass tube opposite to the reference electrode port. Branch pipes of the working electrode port, the reference electrode port, and the auxiliary electrode port have a diameter between 20 and 30 mm and a length between 50 and 300 mm.

In a class of this embodiment, the working electrode is made of a material of a carbon steel, a stainless steel, or copper having a polished surface. The reference electrode is a saturated calomel electrode or a silver-silver chloride electrode. The auxiliary electrode is a platinum electrode.

In a class of this embodiment, the working electrode and the auxiliary electrode are fixed in the working electrode port and the auxiliary electrode port, respectively, by using rubber stoppers. The reference electrode is fixed in the reference electrode port by using a salt bridge pipe. A distance between the working electrode and a capillary tube passing through the salt bridge of the reference electrode is 0.5-1 mm.

In accordance with another embodiment of the invention, there is provided a method for evaluating a corrosion inhibitor for a circulating cooling water system, the method comprising steps as follows:

1) providing a water sample for testing or artificially preparing a corrosive solution: providing the water sample comprising standing the water sample for precipitating, and collecting a supernatant for testing; preparing the corrosive solution comprising collecting a solute into a beaker, adding distilled water into the beaker to dissolve the solute and obtain a mixture, transferring the mixture into a volumetric flask after a temperature thereof being cooled to a room temperature, and replenishing distilled water into the volumetric flask to a constant volume to yield the corrosive solution;

2) preparing electrodes: preparing an auxiliary electrode comprising washing a platinum electrode using distilled water, acetone, and distilled water, respectively; preparing a reference electrode comprising adding 1-1.5 g of agar and 10 g of potassium chloride powder into 30 mL of distilled water to yield a mixture, heating the mixture until boiling and solid therein being dissolved, using a pipette bulb to adsorb the mixture into a salt bridge tube, inserting a saturated calomel electrode or a silver-silver chloride electrode into the mixture in the salt bridge tube to obtain the reference electrode, and preserving the reference electrode after being cooled and condensed; preparing a working electrode comprising shaping a material of a carbon steel, a stainless steel, or copper into a cylinder or a rectangular column, welding the working electrode with a copper wire provided with an insulating rubber, employing a resin material to cover a surface of the working electrode and leave an exposed area of 0.5-2 $cm^2$, polishing the surface of the working electrode by a sand paper, washing the surface of the working electrode by using distilled water, acetone, and distilled water, respectively;

3) inputting the prepared water sample for testing or the artificially prepared corrosive solution in step 1) into a circulating cooling water tank; starting a heating rod to heat the prepared water sample for testing or the artificially prepared corrosive solution to a preset temperature to be simulated; fixing the auxiliary electrode, the reference electrode, and the working electrode into corresponding branch pipes of a five-port glass tube, respectively; connecting a electrochemical workstation to the auxiliary electrode, the reference electrode, and the working electrode via three wiring clamps, respectively; turning on a power switch of the electrochemical workstation; and starting a control program of the electrochemical workstation of a host computer;

4) starting a circulating water pump, adjusting a flow regulating button of a flowmeter to control a flow at 1-10 L/min; opening a testing interface for an open-circuit-potential of the control program of the electrochemical workstation, setting a frequency of data collection at 1-5 Hz and an operation time of 30-120 min; opening a testing interface for an AC impedance of the control program of the electrochemical workstation after the open-circuit-potential being stable at ±0.5 mV, and setting a scanning frequency range of $10^{-2}$-$10^5$ Hz;

5) collecting data from the auxiliary electrode the reference electrode, and the working electrode and charting a Nyquist plot according thereto, fitting and calculating a charge transfer resistance $R_t$ of a total electrochemical reaction by using an electrochemical impedance analysis software;

6) collecting the corrosion inhibitor to be tested to prepare a water sample comprising the corrosion inhibitor, inputting the water sample comprising the corrosion inhibitor into a circulating cooling water tank; repeating step 3) and step 4); collecting data from the auxiliary electrode, the reference electrode, and the working electrode, charting the Nyquist plot according thereto; fitting and calculating a charge transfer resistance $R_t'$ of a total electrochemical reaction in the presence of the corrosion inhibitor by using the electrochemical impedance analysis software;

7) calculating corrosion inhibition efficiency $\eta$ of the corrosion inhibitor according to the following formula:

$$\eta = 1 - \frac{R_t}{R_t'}$$

in which, $R_t$ represents the charge transfer resistance of the total electrochemical reaction excluding a corrosion inhibitor, $R_t'$ represents the charge transfer resistance of the total electrochemical reaction in the presence of the corrosion inhibitor, and $\eta$ represents the corrosion inhibition efficiency.

Principle of the invention is summarized as follows.

In the circulating cooling water simulator, the flow velocity and the temperature of the water are controlled to be almost the same as those of an actual working condition. The simulator is provided with a three-electrode system to collect signals of the electric potential and the electric current. The scale formation or corrosion is well known by analyzing the AC impedance spectroscopy in the presence of the corrosion inhibitor or no corrosion inhibitor involved, based on which to calculate the scale inhibition efficiency or the corrosion inhibition efficiency of the corrosion inhibitor.

The circulating cooling water simulator is provided with the five-port glass tube for fixing the electrodes. The water outlet and the water inlet are disposed on two ends of the five-port glass tube, and three other ports are arranged on two sides of the five-port glass tube for fixing electrodes, that is, the working electrode, the reference electrode, and the auxiliary electrode. The working electrode is made of metal materials for testing. The working electrode is arranged on an opposite side to the reference electrode. The distance between the working electrode and the capillary tube passing through the salt bridge of the reference electrode is 0.5-1 mm, so that ions of the reference electrode are prevented from into the tested solution, and it is more convenient to collect stable signals of the electric potential and the electric current. The distance between the working electrode and the auxiliary electrode is between 10 and 30 mm for collecting the electric current between the working electrode and the auxiliary electrode.

The electric potential and data of the electrodes are collected in an operation condition of the whole device, and the flow velocity of the water on the surface of the working electrode is capable of simulating that of the actual working condition. During the test of the corrosion inhibition performance of the corrosion inhibitor, the solution for testing is the actual water sample, or the artificially prepared corrosive solution (such as a sulfuric acid solution, a hydrochloric acid solution, or a solution of sodium chloride salt). In the presence of the corrosion inhibitor, the corrosion inhibitor is absorbed on the surface of the working electrode to form a protective membrane, thereby affecting signals of the electric potential and the electric current. The corrosion inhibition efficiency is calculated by analyzing the AC impedance spectroscopy in the presence of the corrosion inhibitor or without the corrosion inhibitor.

Advantages of the invention are summarized as follows:
1) The device for evaluating the corrosion inhibitor for the circulating cooling water system of the invention is provided with the five-port glass tube that is capable of simulating the hydraulic condition of the circulating cooling water and fixing the three electrodes. The device and the method of the invention achieve a good combination of the method for testing the AC impedance spectroscopy and testing condition of dynamic circulating cooling water. The device is capable of simulating the temperature and the flow velocity of the circulating cooling water system, and can fast evaluate the corrosion inhibition performance of the corrosion inhibitor.
2) The method for evaluating the corrosion inhibitor for the circulating cooling water system of the invention has a simple operation and is timesaving. The method is capable of simulating the water velocity and temperature of the actual working condition of the circulating cooling water, thereby providing an effective evaluating method for a development, selection, and combination of the corrosion inhibitors according to different water conditions in the circulating cooling water system.
3) During the test of the method and the device of the invention, a test piece is not necessary to be taken off or treated. Data are collected during the operation of the device, the corrosion inhibition performance are analyzed by analyzing the AC impedance spectroscopy. The data from the test have a high accuracy and strong stability.

BRIEF DESCRIPTION OF THE DRAWINGS

The invention is described hereinbelow with reference to the accompanying drawings, in which.

Figure 1:
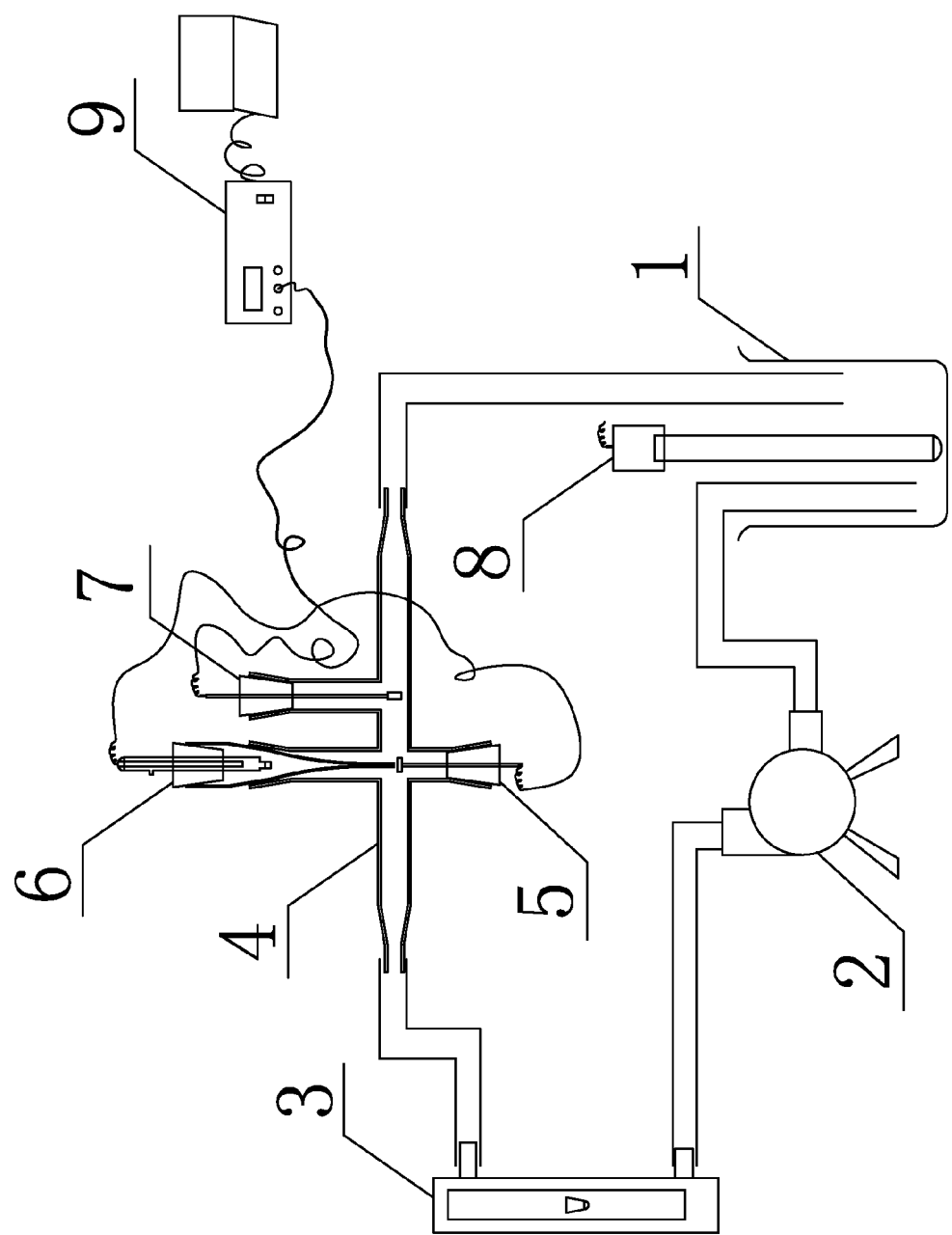
FIG. 1 is a structure diagram of a device for evaluating a corrosion inhibitor for a circulating cooling water system in accordance with one embodiment of the invention.

In the drawings, the following reference numbers are used:
1. Circulating cooling water tank; 2. Circulating water pump; 3. Flowmeter; 4. Five-port glass tube; 401. Water inlet; 402. Water outlet; 403. Working electrode port; 404. Reference electrode port; 405. Auxiliary electrode port; 5. Working electrode; 6. Reference electrode; 7. Auxiliary electrode; 8. Heating rod; and 9. Electrochemical workstation.

DETAILED DESCRIPTION OF THE EMBODIMENTS

For further illustrating the invention, experiments detailing a device and a method for evaluating a corrosion inhibitor for a circulating cooling water system are described below. It should be noted that the following examples are intended to describe and not to limit the invention.

Figure 2:
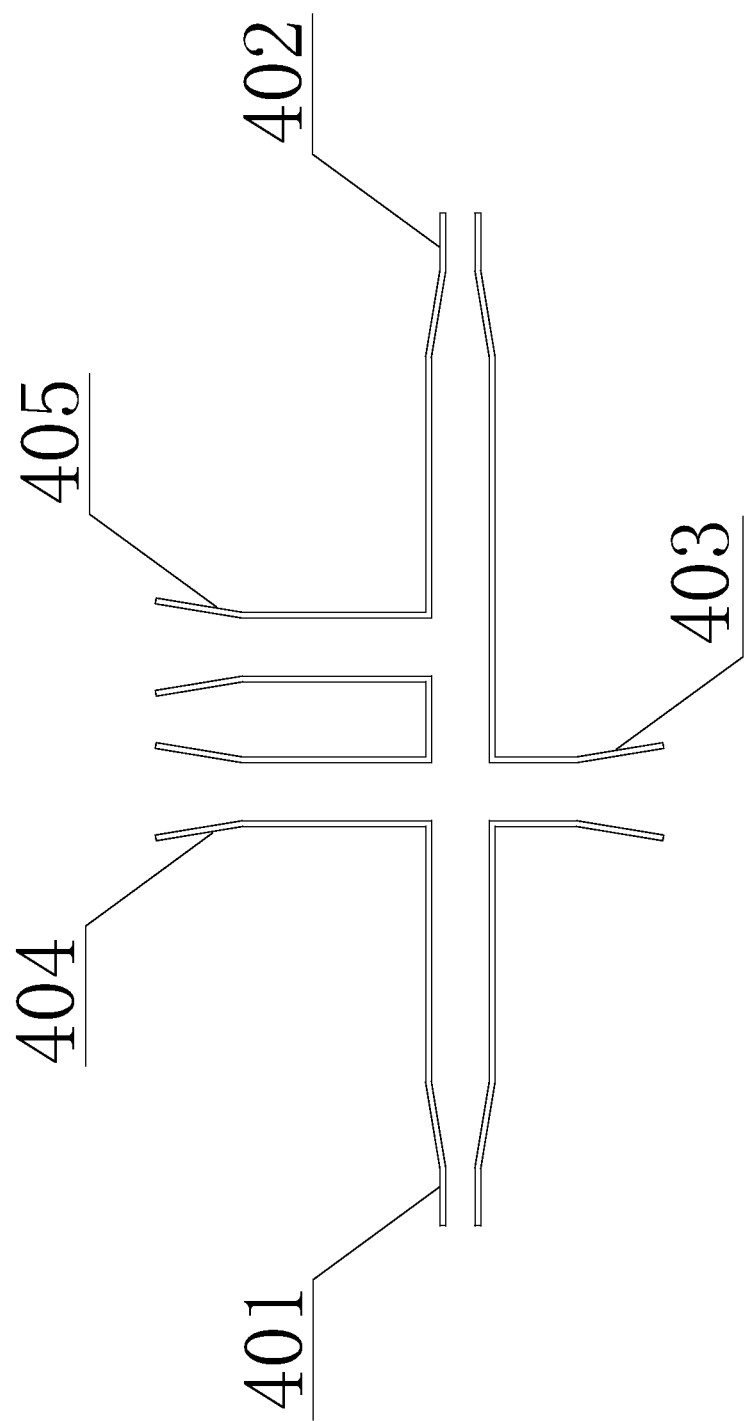
FIG. 2 is a structure diagram of a five-port glass tube in accordance with one embodiment of the invention.

As shown in FIGS. 1-2, a device for evaluating a corrosion inhibitor for a circulating cooling water system, the device comprises: a circulating cooling water tank 1, a circulating water pump 2, a flowmeter 3, a five-port glass tube 4, a working electrode 5, a reference electrode 6, an auxiliary electrode 7, a heating rod 8, and an electrochemical workstation 9. The circulating water pump 2 is connected to the circulating cooling water tank 1 via a pipe. The heating rod 8 is fixed inside the circulating cooling water tank 1. A water inlet of the flowmeter 3 is connected to the circulating water pump 2; and a water outlet of the flowmeter 3 is connected to a water inlet 401 of the five-port glass tube 4 via a pipe. The five-port glass tube 4 comprises: the water inlet 401, a water outlet 402, a working electrode port 403, a reference electrode port 404, and an auxiliary electrode port 405. The working electrode 5, the reference electrode 6, and the auxiliary electrode 7 are mounted in the working electrode port 403, the reference electrode port 404, and the auxiliary electrode port 405, respectively. The working electrode 5 is made of a material of a carbon steel, a stainless steel, or copper having a polished surface. The reference electrode 6 is a saturated calomel electrode or a silver-silver chloride electrode. The auxiliary electrode 7 is a platinum electrode. The working electrode 5 and the auxiliary electrode 7 are fixed in the working electrode port 403 and the auxiliary electrode port 405, respectively, by using rubber stoppers. The reference electrode 6 is fixed in the reference electrode port 404 by using a salt bridge pipe. A distance between the working electrode 5 and a capillary tube passing through the salt bridge of the reference electrode 6 is 0.5-1 mm. The water outlet 402 of the five-port glass tube 4 is connected to the circulating cooling water tank 1 via a pipe. The working electrode 5, the reference electrode 6, and the auxiliary electrode 7 are connected to the electrochemical workstation 9. The electrochemical workstation 9 is connected to a host computer.

The five-port glass tube 4 is a glass tube having a diameter between 20 and 30 mm and a length between 300 and 500 mm. The water inlet 401 and the water outlet 402 of the five-port glass tube 4 are arranged on two horizontal ends of the five-port glass tube 4, and the water inlet 401 and the water outlet 402 of the five-port glass tube 4 have a diameter between 10 and 20 mm and a length between 30 and 50 mm. The reference electrode port 404 and the auxiliary electrode port 405 are arranged on one side of the five-port glass tube 4. A distance between a branch pipe of the reference electrode port 404 and a branch pipe of the auxiliary electrode port 405 is 10-30 mm. The working electrode port 403 is arranged on the other side of the five-port glass tube 4 opposite to the reference electrode port 404. Branch pipes of the working electrode port 403, the reference electrode port 404, and the auxiliary electrode port 405 have a diameter between 20 and 30 mm and a length between 50 and 300 mm.

Specifically, a device for evaluating a corrosion inhibitor for a circulating cooling water system comprises: a circulating cooling water tank 1, a circulating water pump 2, a flowmeter 3, a five-port glass tube 4, a working electrode 5, a reference electrode 6, an auxiliary electrode 7, a heating rod 8, and an electrochemical workstation 9. A water inlet of the circulating water pump 2 communicates with a solution in the circulating cooling water tank 1 via a silicone tube. The circulating cooling water tank 1 herein is a 1000 mL beaker, the circulating water pump 2 is an MP-20R water pump manufactured by Shanghai Jiaxing Pumps Co., Ltd. The heating rod 8 is fixed inside the circulating cooling water tank 1. The heating rod 8 is a 300 w heating rod device manufactured by Aqua Zonic Company; and the heating rod is used to control a temperature of the solution in the circulating cooling water tank 1. A water inlet of the flowmeter 3 is connected to a water outlet of the circulating water pump 2 via a pipe. The flowmeter 3 is a LZB-10 flowmeter produced by Dongtai Dongxing Instrument Factory; and the flowmeter 3 is used to control a flow velocity of the solution. A water outlet of the flowmeter 3 is connected to a water inlet 401 of the five-port glass tube 4 via a silicone tube. A water outlet 402 of the five-port glass tube 4 is connected to the circulating cooling water tank 1 via a silicone tube. The working electrode 5, the reference electrode 6, and the auxiliary electrode 7 are connected to the electrochemical workstation 9 via copper wires. The electrochemical workstation 9 herein is a CS 310 electrochemical workstation 9 produced by Wuhan Corrtest Instrument Co., Ltd. The electrochemical workstation 9 is connected to a host computer, as shown in FIG. 1. The silicone tubes herein are Φ15*2 silicone tubes produced by Guansheng silicone products Co., Ltd. The solution inside the circulating cooling water tank 1 is extracted by the circulating water pump 2, passes through the flowmeter 3, the five-port glass tube 4, and finally through the water outlet 402 of the five-port glass tube 4 and the silicone tube back into the circulating cooling water tank 1.

The five-port glass tube 4 comprises: a water inlet 401, a water outlet 402, a working electrode port 403, a reference electrode port 404, and an auxiliary electrode port 405. The working electrode 5, the reference electrode 6, and the auxiliary electrode 7 are mounted in the working electrode port 403, the reference electrode port 404, and the auxiliary electrode port 405, respectively. The five-port glass tube 4 is a glass tube having a diameter of 26 mm and a length of 400 mm. The water inlet 401 and the water outlet 402 of the five-port glass tube 4 are arranged on two horizontal ends of the five-port glass tube 4; and the water inlet 401 and the water outlet 402 of the five-port glass tube 4 have a diameter of 16 mm and a length of 40 mm. The reference electrode port 404 and the auxiliary electrode port 405 are arranged on one side of the five-port glass tube 4. A distance between a branch pipe of the reference electrode port 404 and a branch pipe of the auxiliary electrode port 405 is 20 mm. The working electrode port 403 is arranged on the other side of the five-port glass tube 4 opposite to the reference electrode port 404. A diameter of branch pipes of the working electrode port 403, the reference electrode port 404, and the auxiliary electrode port 405 is 26 mm. A length of the branch pipes of the reference electrode port 404 and the auxiliary electrode port 405 is 120 mm, and a length of the branch pipe of the working electrode is 50 mm.

The working electrode 5 is made of a material of carbon steel, stainless steel, or copper having a polished surface. A 20# carbon steel working electrode produced by Wuhan Corrtest Instrument Co., Ltd is adopted. The reference electrode 6 is a saturated calomel electrode produced by Shanghai Ruosull Technology Co., Ltd. The auxiliary electrode 7 is a 260 conductance electrode produced by Shanghai Ruosull Technology Co., Ltd. The working electrode 5 and the aux-iliary electrode 7 are fixed in the working electrode port 403 and the auxiliary electrode port 405, respectively, by using rubber stoppers. The reference electrode 6 is fixed in the reference electrode port 404 by using a salt bridge pipe. A distance between the working electrode 5 and a capillary tube passing through the salt bridge of the reference electrode 6 is 0.5 mm.

A method for evaluating a corrosion inhibitor by using the above device, the method comprising the following steps:

1) Preparation of a Water Sample for Testing:

The water sample used to test the corrosion inhibition performance of the corrosion inhibitor herein is an actual water sample collected from a wastewater treatment plant in Nanjing. The wastewater of the wastewater treatment plant is mainly from domestic wastewater. The wastewater after a biochemical treatment is clear, and the water quality indexes are as shown in Table 1.

TABLE 1

Water quality indexes of an actual water sample

| COD | N—$NH_4^+$ | N—$NO_3^-$ | pH | Chromaticity | Conductivity | $Ca^{2+}$ | $Mg^{2+}$ |
|---|---|---|---|---|---|---|---|
| 53.0 mg/L | 0.45 mg/L | 19.6 mg/L | 7.1 | 3 times | 638 μs/cm | 53.0 mg/L | 11.3 mg/L |

Standing the water sample for precipitating for 4 hours, collect a supernatant for testing. Or artificially prepare a corrosive solution for testing.

2) Electrodes preparation: prepare the auxiliary electrode 7 by adopting a platinum electrode, wash the platinum electrode by using distilled water, acetone, and distilled water one by one. Prepare the working electrode 5 by adopting the material of the carbon steel, shape the 20# carbon steel working electrode into a cylinder; weld the working electrode with a copper wire provided with an insulating rubber; cover a resin material on a surface of the working electrode to leave an exposed area of 0.5-2 $cm^2$; polish the surface of the working electrode by a 2000 sand paper; wash the surface of the working electrode by using distilled water, acetone, and distilled water one by one; and preserve the working electrode. Prepare the reference electrode 6 by adopting the saturated calomel electrode, collect 1.2 g of agar and 10 g of potassium chloride powder into 30 mL of distilled water to yield a mixture; heat the mixture until boiling and solid therein being dissolved; use a pipette bulb to adsorb the mixture into a glass salt bridge tube to a certain height, insert the saturated calomel electrode into the mixture in the glass salt bridge tube to obtain the reference electrode, and preserve the reference electrode after being cooled and condensed.

3) Input 1 L of the prepared water sample for testing in step 1 into a circulating cooling water tank 1; start the heating rod 8 to heat the prepared water sample to 40° C. Fix the auxiliary electrode 7, the reference electrode 6, and the working electrode 5 into corresponding branch pipes of the five-port glass tube 4, respectively. Connect the electrochemical workstation 9 to the auxiliary electrode 7, the reference electrode 6, and the working electrode 5 via three wiring clamps, respectively. Turn on a power switch of the electrochemical workstation 9, and start a control program of the electrochemical workstation 9 of a host computer.

4) Start the circulating water pump 2, adjust a flow regulating button of the flowmeter 3 to control a flow at 1-10 L/min. Open a testing interface for an open-circuit-potential of the control program of the electrochemical workstation 9; set a frequency of data collection at 1 Hz and an operation time of 60 min. Open a testing interface for an AC impedance of the control program of the electrochemical workstation 9 after the open-circuit-potential is stable at ±0.5 mV, and set a scanning frequency range of between $10^{-2}$ and $10^5$ Hz.

5) In condition of no corrosion inhibitor added, collect data from the auxiliary electrode 7, the reference electrode 6, and the working electrode 5, and chart a Nyquist plot according thereto. Fit and calculate a charge transfer resistance $R_t$ of a total electrochemical reaction by using electrochemical impedance analysis software.

6) Provide a 1 L volumetric flask, add 500 mL of the water sample into the volumetric flask. Collect 1 mL of a corrosion inhibitor solution for controlling a dosage of the corrosion inhibitor at 40 mg/L, and replenish the water sample into the volumetric flask to a constant volume. Input water sample comprising the corrosion inhibitor into the circulating cooling water tank 1; repeat step 3) and step 4). Collect data from the auxiliary electrode 7, the reference electrode 6, and the working electrode 5 and chart the Nyquist plot according thereto. Fit and calculate a charge transfer resistance $R_t'$ of a total electrochemical reaction in the presence of the corrosion inhibitor by using the electrochemical impedance analysis software; and 7) calculating a corrosion inhibition efficiency η of the corrosion inhibitor according to the following formula:

$$\eta = 1 - \frac{R_t}{R_t'}$$

in which, $R_t$ represents the charge transfer resistance of the total electrochemical reaction in the condition of no corrosion inhibitor added, $R_t'$ represents the charge transfer resistance of the total electrochemical reaction in the presence of the corrosion inhibitor, and η represents the corrosion inhibition efficiency. Herein corrosion inhibition performances of 1-hydroxy ethylidene-1,1-diphosphonic acid (HEDP), amino trimethylene phosphonic acid (ATMP), 2-phosphonic acid-1,2,4-Tricarboxylic acid butane (PBTCA) are tested by using a dosage of 40 mg/L, results are shown in Table 2.

TABLE 2

Testing results of corrosion inhibition performance of three corrosion inhibitors

| Corrosion inhibitor | HEDP | ATMP | PBTCA |
| --- | --- | --- | --- |
| Corrosion efficiency (%) | 79.8 | 85.6 | 83.7 |

The five-port glass tube 1 herein is capable of simulating a hydraulic condition of the circulating cooling water and fixing the three electrodes. The device and the method of the invention achieve a good combination of the method for testing the AC impedance spectroscopy and testing condition of dynamic circulating cooling water. The device is capable of simulating the temperature and the flow velocity of the circulating cooling water system, and can fast evaluate the corrosion inhibition performance of the corrosion inhibitor. Data from the testing have high accuracy and strong reliability.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for evaluating a corrosion inhibitor, the device comprising:
   a) a circulating cooling water tank (1);
   b) a circulating water pump (2);
   c) a flowmeter (3), the flowmeter (3) comprising a water inlet and a water outlet;
   d) a five-port glass tube (4), the five-port glass tube (4) comprising a water inlet (401), a water outlet (402), a working electrode port (403), a reference electrode port (404), and an auxiliary electrode port (405);
   e) a working electrode (5);
   f) a reference electrode (6);
   g) an auxiliary electrode (7);
   h) a heating rod (8); and
   i) an electrochemical workstation (9);

wherein
   the circulating water pump (2) is connected to the circulating cooling water tank (1) via a first pipe;
   the heating rod (8) is fixed inside the circulating cooling water tank (1);
   the water inlet of the flowmeter (3) is connected to the circulating water pump (2); the water outlet of the flowmeter (3) is connected to the water inlet (401) of the five-port glass tube (4) via a second pipe;
   the working electrode (5), the reference electrode (6), and the auxiliary electrode (7) are mounted in the working electrode port (403), the reference electrode port (6), and the auxiliary electrode port (6), respectively;
   the water outlet (402) of the five-port glass tube (4) is connected to the circulating cooling water tank (1) via a third pipe;
   the working electrode (5), the reference electrode (6), and the auxiliary electrode (7) are connected to the electrochemical workstation (9); and
   the electrochemical workstation (9) is connected to a host computer.

2. The device of claim 1, wherein
   the five-port glass tube (4) is a glass tube having a diameter between 20 and 30 mm and a length between 300 and 500 mm; the water inlet (401) and the water outlet (402) are arranged on two horizontal ends of the five-port glass tube (4), the water inlet (401) and the water outlet (402) of the five-port glass tube (4) have a diameter between 10 and 20 mm and a length between 30 and 50 mm;
   the reference electrode port (404) and the auxiliary electrode port (405) are arranged on one side of the five-port glass tube (4), a distance between a branch pipe of the reference electrode port (404) and a branch pipe of the auxiliary electrode port (405) is between 10 and 30 mm; the working electrode port (403) is arranged on the other side of the five-port glass tube (4) opposite to the reference electrode port (404); and
   branch pipes of the working electrode port (403), the reference electrode port (404), and the auxiliary electrode port (405) have a diameter between 20 and 30 mm and a length between 50 and 300 mm.

3. The device of claim 2, wherein
   the working electrode (5) is made of a material of carbon steel, stainless steel, or copper, each having a polished surface;
   the reference electrode (6) is a saturated calomel electrode or a silver-silver chloride electrode; and
   the auxiliary electrode (7) is a platinum electrode.

4. The device of claim 3, wherein
- the working electrode (5) and the auxiliary electrode (7) are fixed in the working electrode port (403) and the auxiliary electrode port (405), respectively, by using rubber stoppers;
- the reference electrode (6) is fixed in the reference electrode port (404) by using a salt bridge pipe; and
- a distance between the working electrode (5) and a capillary tube passing through the salt bridge of the reference electrode (6) is between 0.5 and 1 mm.

5. The device of claim 1, wherein
- the working electrode (5) is made of a material of carbon steel, stainless steel, or copper, each having a polished surface;
- the reference electrode (6) is a saturated calomel electrode or a silver-silver chloride electrode; and
- the auxiliary electrode (7) is a platinum electrode.

6. The device of claim 5, wherein
- the working electrode (5) and the auxiliary electrode (7) are fixed in the working electrode port (403) and the auxiliary electrode port (405), respectively, by using rubber stoppers;
- the reference electrode (6) is fixed in the reference electrode port (404) by using a salt bridge pipe; and
- a distance between the working electrode (5) and a capillary tube passing through the salt bridge of the reference electrode (6) is between 0.5 and 1 mm.

7. A method for evaluating a corrosion inhibitor, the method comprising the following steps:
- a) providing a water sample for testing or artificially preparing a corrosive solution: providing the water sample comprising standing the water sample for precipitating, and collecting a supernatant for testing; preparing the corrosive solution comprising collecting a solute into a beaker, adding distilled water into the beaker to dissolve the solute and obtain a mixture, transferring the mixture into a volumetric flask after a temperature thereof being cooled to a room temperature, and replenishing distilled water into the volumetric flask to a constant volume to yield the corrosive solution;
- b) preparing electrodes: preparing an auxiliary electrode (7) comprising washing a platinum electrode using distilled water, acetone, and distilled water, respectively; preparing a reference electrode (6) comprising adding 1-1.5 g of agar and 10 g of potassium chloride powder into 30 mL of distilled water to yield a mixture, heating the mixture until boiling and solid therein being dissolved, using a pipette bulb to adsorb the mixture into a salt bridge tube, inserting a saturated calomel electrode or a silver-silver chloride electrode into the mixture in the salt bridge tube to obtain the reference electrode, and preserving the reference electrode after being cooled and condensed; preparing a working electrode (5) comprising shaping a material of a carbon steel, a stainless steel, or copper into a cylinder or a rectangular column, welding the working electrode with a copper wire provided with an insulating rubber, employing a resin material to cover a surface of the working electrode and leave an exposed area of 0.5-2 cm$^2$, polishing the surface of the working electrode by a sand paper, washing the surface of the working electrode by using distilled water, acetone, and distilled water, respectively;
- c) inputting the prepared water sample for testing or the artificially prepared corrosive solution in step 1) into a circulating cooling water tank (1); starting a heating rod (8) to heat the prepared water sample for testing or the artificially prepared corrosive solution to a preset temperature to be simulated; fixing the auxiliary electrode (7), the reference electrode (6), and the working electrode (5) into corresponding branch pipes of a five-port glass tube (4), respectively; connecting a electrochemical workstation (9) to the auxiliary electrode (7), the reference electrode (6), and the working electrode (5) via three wiring clamps, respectively; turning on a power switch of the electrochemical workstation (9); and starting a control program of the electrochemical workstation (9) of a host computer;
- d) starting a circulating water pump (2), adjusting a flow regulating button of a flowmeter (3) to control a flow at 1-10 L/min; opening a testing interface for an open-circuit-potential of the control program of the electrochemical workstation (9), setting a frequency of data collection at 1-5 Hz and an operation time of 30-120 min; opening a testing interface for an AC impedance of the control program of the electrochemical workstation (9) after the open-circuit-potential being stable at ±0.5 mV, and setting a scanning frequency range between $10^{-2}$ and $10^5$ Hz;
- e) collecting data from the auxiliary electrode (7), the reference electrode (6), and the working electrode (5), and charting a Nyquist plot according thereto, fitting and calculating a charge transfer resistance $R_t$ of a total electrochemical reaction by using an electrochemical impedance analysis software;
- f) collecting the corrosion inhibitor to be tested and preparing a water sample comprising the corrosion inhibitor, inputting the water sample comprising the corrosion inhibitor into a circulating cooling water tank; repeating step 3) and step 4); collecting data from the auxiliary electrode (7), the reference electrode (6), and the working electrode (5), charting a Nyquist plot according thereto; fitting and calculating a charge transfer resistance $R_t'$ of a total electrochemical reaction in the presence of the corrosion inhibitor by using the electrochemical impedance analysis software; and
- g) calculating corrosion inhibition efficiency η of the corrosion inhibitor according to the following formula:

$$\eta = 1 - \frac{R_t}{R_t'}$$

in which, $R_t$ represents the charge transfer resistance of the total electrochemical reaction excluding a corrosion inhibitor, $R_t'$ represents the charge transfer resistance of the total electrochemical reaction in the presence of the corrosion inhibitor, and η represents the corrosion inhibition efficiency.

* * * * *